United States Patent [19]

Felix

[11] Patent Number: 4,612,014

[45] Date of Patent: Sep. 16, 1986

[54] USE OF METAL COMPLEXES OF HYDRAZONES AS PIGMENTS

[75] Inventor: Franz Felix, Münchenstein, Switzerland

[73] Assignee: Ciba-Geigy Corporation, Ardsley, N.Y.

[21] Appl. No.: 782,596

[22] Filed: Sep. 30, 1985

Related U.S. Application Data

[63] Continuation of Ser. No. 470,421, Feb. 28, 1983, abandoned.

[30] Foreign Application Priority Data

Mar. 9, 1982 [CH] Switzerland .................. 1438/82

[51] Int. Cl.$^4$ .................................................. D06P 5/12
[52] U.S. Cl. ............................................ 8/452; 8/920
[58] Field of Search ............ 8/452, 920; 106/288 Q, 106/308 N; 260/439, 558, 438.1; 521/920

[56] References Cited

U.S. PATENT DOCUMENTS

| | | |
|---|---|---|
| 3,630,656 | 12/1971 | Wolfrum .................................. 8/31 |
| 3,988,323 | 10/1976 | L'Eplattenier et al. ............ 542/418 |
| 4,065,481 | 12/1977 | L'Eplattenier et al. ......... 260/438.1 |
| 4,144,258 | 3/1979 | L'Eplattenier et al. ............ 542/418 |

Primary Examiner—Amelia B. Yarbrough
Attorney, Agent, or Firm—Luther A. R. Hall

[57] ABSTRACT

Transition-metal complexes of hydrazones of the formula

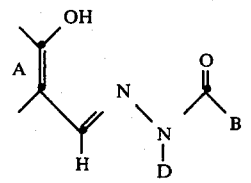

wherein A and B independently of one another are isocyclic or heterocyclic aromatic radicals and D is hydrogen, are suitable for pigmenting high-molecular organic material.

12 Claims, No Drawings

USE OF METAL COMPLEXES OF HYDRAZONES AS PIGMENTS

This application is a continuation, of application Ser. No. 470,421, filed Feb. 28, 1983, now abandoned.

The G.B. Patent Specification No. 1,512,679 describes a process for pigmenting high-molecular organic material by the use of metal complexes of hydrazones of the formula (O)

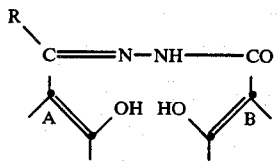

wherein A and B are isocyclic or heterocyclic aromatic radicals, with only one of the radicals A and B being a benzene ring, and R is hydrogen, $C_1$–$C_6$-alkyl or aryl. The use of these pigments results however in dyeings which do not satisfy requirements with respect to colour strength, brilliance, fastness properties and purity of shade.

The present invention relates to a process for pigmenting high-molecular organic material, which process comprises the use of a transition-metal complex of a hydrazone of the formula I

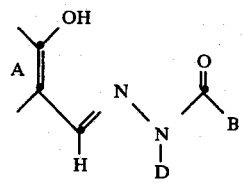

wherein A and B independently of one another are isocyclic or heterocyclic aromatic radicals, and D is hydrogen, and, if B is a phenyl or naphthyl group, D is hydrogen, or a carbonyl group which together with the structural element

forms a phthalimide or naphthalimide group.

As isocyclic or heterocyclic aromatic radicals, A and B can be in particular: unsubstituted or mono- or disubstituted benzene, naphthalene, pyridine, pyrimidine, pyrazolone, quinoline, isoquinoline, pyrazole or coumarin groups. Possible substituents are for example: halogen, $C_1$–$C_6$-alkyl, $C_1$–$C_6$-alkoxy, cyano, nitro, carboxy, $C_2$–$C_7$-alkoxycarbonyl, carbamoyl, unsubstituted phenyl, phenoxy, phenylcarbamoyl, benzoylamino; or phenyl, phenoxy, phenylcarbamoyl or benzoylamino each substituted by halogen, $C_1$–$C_6$-alkyl or $C_1$–$C_6$-alkoxy.

Halogen can be for example fluorine, chlorine or bromine, preferably chlorine or bromine.

$C_1$–$C_6$-Alkyl can be straight-chain or branched-chain, and is in particular: methyl, ethyl, isopropyl, sec-butyl, tert-butyl, tert-amyl or n-hexyl.

$C_1$–$C_6$-Alkoxy can be straight-chain or branched-chain, and is especially: methoxy, ethoxy, propoxy, isopropoxy, n-butoxy, n-pentoxy or n-hexyloxy.

$C_2$–$C_7$-Alkoxycarbonyl can be straight-chain or branched-chain, and is particularly: methoxycarbonyl, ethoxycarbonyl, n-propoxycarbonyl, isopropoxycarbonyl, tert-butoxycarbonyl, n-pentoxycarbonyl or n-hexyloxycarbonyl.

When the substituents on A and B are substituted phenyl, phenoxy, phenylcarbamoyl and benzoylamino, they can be: 4-chlorophenyl, 2,4-dichlorophenyl, 4-methylphenylcarbamoyl, 3,4-dichlorophenylcarbamoyl, 4-methoxyphenylcarbamoyl, 4-methylbenzoylamino, 4-chlorobenzoylamino, 3-chloro-4-methylbenzoylamino and 4-methoxybenzoylamino.

Suitable transition metals are in particular ions having a double positive charge, such as $Ni^{2+}$, $Cu^{2+}$, $Zn^{2+}$ and $Co^{2+}$, especially however $Ni^{2+}$ and $Cu^{2+}$.

To 1 metal ion there can be 1 or 2 radicals of a hydrazone of the formula I, so that 1:1- or 1:2-metal complexes can be present. In the process according to the invention, however, 1:1-copper complexes or especially 1:2-nickel complexes of a hydrazone of the formula I are preferably used.

The 1:1-metal complexes can be monomeric or, particularly those of $Cu^{2+}$, dimeric. In the case of the monomeric 1:1-metal complexes, the fourth coordination position of the metal ion can be occupied by an additional ligand, such as $H_2O$, $NH_3$ or $CH_3COO^{\ominus}$. This depends largely on the conditions of production of the metal complexes, and on the nature of the employed metal-releasing agent. Monomeric 1:1-metal complexes with acetate groups can be represented by the following formula

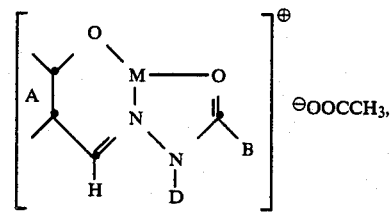

wherein M is the metal atom, and the symbols A, B and D have the meanings defined in the foregoing.

In the process according to the invention, there is preferably used a 1:1- or 1:2-nickel complex or 1:1-copper complex, especially however a 1:2-nickel or 1:1-copper complex of a hydrazone of the formula II

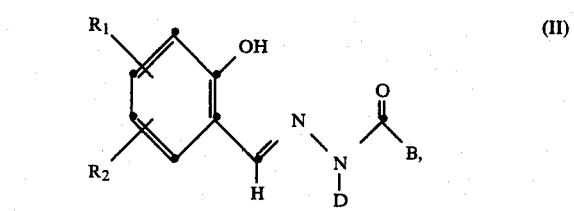

or of the formula III

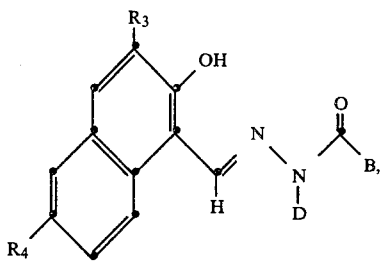 (III)

wherein $R_1$ and $R_2$ independently of one another are each hydrogen, chlorine, bromine, $C_1$-$C_3$-alkyl, $C_1$-$C_3$-alkoxy, cyano or nitro, and $R_3$ is hydrogen, carboxy, $C_2$-$C_4$-alkoxycarbonyl, carbamoyl, or phenylcarbamoyl which is unsubstituted or monosubstituted by $C_1$-$C_3$-alkyl, $C_1$-$C_3$-alkoxy, chlorine or bromine, and $R_4$ is hydrogen, chlorine, bromine or $C_1$-$C_3$-alkoxy, and B is unsubstituted phenyl or naphthyl, or phenyl or naphthyl which are each substituted by one or two identical or different substituents from the group comprising $C_1$-$C_3$-alkyl, $C_1$-$C_3$-alkoxy, chlorine, bromine, nitro, phenyl, phenoxy, chlorophenoxy, bromophenoxy, methylphenoxy, methoxyphenoxy, benzoylamino, methylbenzoylamino, methoxybenzoylamino, chlorobenzoylamino and bromobenzoylamino, and D is hydrogen, or a carbonyl group which together with the structural element

forms a phthalimide or naphthalimide group.

Used with particular preference in the process according to the invention is the 1:1- or 1:2-nickel complex or 1:1-copper complex of a hydrazone of the formula II or III wherein $R_1$ and $R_2$ independently of one another are each hydrogen, chlorine or bromine, and $R_3$ is hydrogen, carboxy, methoxycarbonyl, carbamoyl or phenylcarbamoyl, and $R_4$ is hydrogen or bromine; B is unsubstituted phenyl or naphthyl, or phenyl or naphthyl each substituted by one or two identical or different substituents from the group comprising methyl, methoxy, chlorine, bromine, nitro or phenyl; and D is hydrogen.

Especially preferred in the process according to the invention is the use of the 1:1- or 1:2-nickel complex or 1:1-copper complex of a hydrazone of the formula III wherein $R_3$ is hydrogen, carboxy or phenylcarbamoyl; and $R_4$ is hydrogen or bromine; D is hydrogen; and B is phenyl which is unsubstituted or monosubstituted by chlorine, bromine, methyl, methoxy or nitro.

More especially preferred is the use of the 1:1- or 1:2-nickel complex or 1:1-copper complex of a hydrazone of the formula II wherein $R_1$ and $R_2$ are chlorine; B is phenyl substituted by methyl; and D is hydrogen.

Very particularly preferred is the use of the 1:1- or 1:2-nickel complex or 1:1-copper complex of a hydrazone of the formula III wherein $R_3$, $R_4$ and D are each hydrogen; and B is unsubstituted phenyl.

The compounds used in the process according to the invention are novel so far as they are 1:1- or 1:2-nickel complexes or 1:1-copper complexes of hydrazones of the formula I wherein A is a heterocyclic aromatic radical, and the symbols B and D are as defined in the foregoing; or of hydrazones of the formula II and III, wherein $R_1$ and $R_2$ are both either chlorine or bromine, $R_3$ is hydrogen, carboxy, $C_2$-$C_7$-alkoxycarbonyl, carbamoyl or phenylcarbamoyl, $R_4$ is hydrogen or bromine, B is unsubstituted phenyl or naphthyl, or phenyl or naphthyl each substituted by $C_1$-$C_6$-alkyl, $C_1$-$C_6$-alkoxy, halogen, nitro, phenyl, phenoxy, halophenoxy, $C_7$-$C_{12}$-alkylphenoxy, $C_7$-$C_{12}$-alkoxyphenoxy, benzoylamino, $C_8$-$C_{13}$-alkylbenzoylamino, $C_8$-$C_{13}$-alkoxybenzoylamino or halobenzoylamino, and D is hydrogen, or a carbonyl group which together with the structural element

forms a phthalimide or naphthalimide group; $R_3$ or $R_4$ having to have a meaning other than hydrogen when D is hydrogen and B is unsubstituted phenyl.

Both the known and the novel transition-metal complexes of the hydrazones of the formula I can be produced by condensing a compound of the formula IV

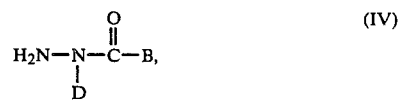 (IV)

wherein D and B have the meanings defined in the foregoing, with an aldehyde of the formula V

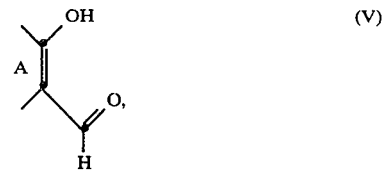 (V)

or with an aldimine of the formula VI

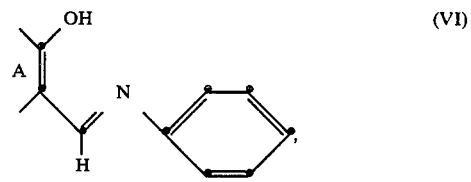 (VI)

wherein A is as defined in the foregoing, in a solvent; and adding a metal-releasing agent either during or after the condensation reaction.

Both the 1:1- and the 1:2-metal complexes can be produced by this process. Electron-attracting groups in the radical A or B and an excess of metal-releasing agent as a rule promote the formation of the 1:1-metal complex.

Suitable metal-releasing agents are in particular M-formiate, M-stearate or M-acetylacetonate, and especially M-acetate, the symbol M being the transition metal.

The solvent used is an organic solvent, particularly however water. It is also possible to use mixtures of solvents. The use of water as solvent is novel, and hence likewise forms subject matter of the invention.

Organic solvets which are suitable are especially: ethanol, butanol, acetic acid, dioxane, dimethylformamide, ethyl cellosolve, ethylene glycol monomethyl ether or N-methylpyrrolidone.

The condensation reaction and the treatment with the metal-releasing agent are performed preferably at elevated temperature, particularly between 50° C., especially 80° C., and the boiling point of the employed solvent.

The metal complexes of the hydrazones of the formula I can be readily isolated by filtration. Any impurities present can be removed by washing.

The compounds of the formulae IV, V and VI are known, and can be produced by known processes.

High-molecular organic materials which can be pigmented with the transition-metal complexes of hydrazones of the formula I are for example: cellulose ethers and cellulose esters, such as ethyl cellulose, nitrocellulose, cellulose acetate, cellulose butyrate, natural resins or synthetic resins, such as polymerisation resins or condensation resins, for example aminoplastics, especially urea-formaldehyde resins and melamine-formaldehyde resins, alkyd resins, phenoplastics, polycarbonates, polyolefins, such as polystyrene, polyvinyl chloride, polyethylene, polypropylene, polyacrylonitrile, polyacrylic acid esters, polyamides, polyurethanes or polyesters, rubber, casefin, silicones and silicone resins, singly or in admixture with each other.

It is in this respect not important whether the said high-molecular compounds are in the form of plastics or of melts; or in the form of spinning solutions, lacquers, paints or printing pastes. Depending on the purpose of application, it is advantageous to use the novel pigments as toners, or in the form of preparations. The metal complex of the hydrazone of the formula I is used in an amount preferably of 0.1 to 10% by weight, relative to the high-molecular organic material to be pigmented.

The pigments can be used in the form they occur in after synthesis. In the slightly ground state, they give opaque dyeings. They can however be subjected to intensive grinding, and there are then obtained transparent pigments which are particularly suitable for producing deeply coloured metal-effect lacquer finishes.

When the pigments to be used according to the invention are incorporated into plastics or fibres, they stabilise these against the effects of light and weather. Objects produced from the dyed substrates are distinguished by a longer service life.

In cases where the pigments to be used according to the invention are incorporated into light-stabilised, high-molecular, organic material, the light stability of the material is as a rule not impaired.

A synergistic improvement in the stability to light can in some cases be observed.

The dyeings obtained are characterised by good general fastness properties, in particular by excellent fastness to light, heat, weather, cross-lacquering and migration, and by a brilliance of shade unexpectedly high for metal complexes, as well as high colouring strength and good dispersibility. The pigments have negligible effect on the mechanical properties of the substrates; in particular, they do not affect the distortion properties of plastics components. The pigmented fibres exhibit in general a high level of fastness.

The following Examples illustrate the invention. The term 'parts' denotes parts by weight, and percentages are percent by weight.

EXAMPLE 1

65 parts of stabilised polyvinyl chloride, 35 parts of dioctyl phthalate and 0.2 part of a finely divided 1:2-nickel complex from the benzoylhydrazone of the formula VII

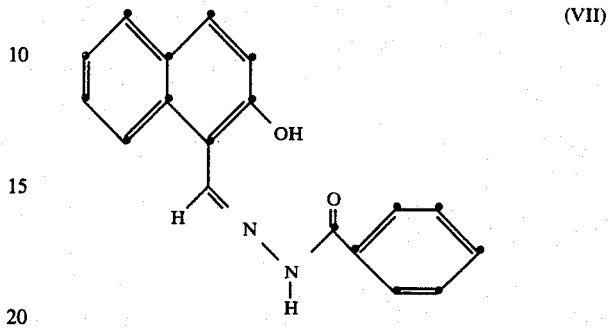

are mixed together, and the mixture is rolled on a two-roller calendering machine for 7 minutes at 160° C. The sheet obtained is dyed yellow and has very good fastness to light and to migration.

PRODUCTION OF THE FINELY DIVIDED FORM OF THE 1:2-NICKEL COMPLEX 25 parts of the 1:2-nickel complex, 100 parts of finely ground sodium chloride and 30 parts of diacetone alcohol are kneaded together for 5 hours, with cooling, in a laboratory kneader. The mixture is introduced into 4000 parts by volume of water, and the formed suspension is filtered off. The isolated pigment is washed with water, and it is subsequently dried in vacuo at 80° C.

EXAMPLE 2

10 g of titanium dioxide and 2 g of a 1:2-nickel complex from the benzoylhydrazone of the formula VII are ground, in a ball mill for 48 hours, with 88 g of a mixture of 26.4 g of coconut oil fatty acid modified alkyd resin, 24.0 g of melamine-formaldehyde resin (50% solid content), 8.8 g of ethylene glycol monomethyl ether and 28.8 g of xylene. When this lacquer is sprayed onto an aluminium sheet, preliminarily dried for 30 minutes at room temperature, and then stoved at 120° C. for 30 minutes, there is obtained a yellow lacquer finish which has a good colour strength, and which is distinguished by excellent fastness to over-lacquering, light and weather.

EXAMPLE 3

4 parts of the finely divided pigment according to Example 1 are stirred into 20 parts of solvent of the following composition: 50 parts of Solvesso 150 ® (mixture of aromatic hydrocarbons), 15 parts of butyl acetate, 5 parts of Exkin II ® (leveling agent based on ketoxime), 25 parts of methyl-isobutyl ketone, and 5 parts of silicone oil (1% in Solvesso 150 ®). When the complete fine dispersion has been obtained (in about 15–60 minutes depending on the type of stirring), the binders are added, namely: 48.3 parts of Baycryl L 530 ® (acrylic resin) [51% in xylene/butanol 3:1] and 23.7 parts of Maprenal TTX ® (melamine resin) [55% in butanol]. After a short period of homogenisation, the lacquer is applied by customary methods, such as spraying and immersion, or, particularly for the continuous coating of metal sheets, by the "coil-coating" process;

and subsequently stoved (stoving for 30 minutes at 130° C.). The resulting yellow lacquer coatings are distinguished by very good rheology, a high gloss and a good fine dispersion of the pigment, as well as by good fastness to weather.

EXAMPLE 4

2 g of a 1:2-nickel complex from the benzoylhydrazone of the formula VII are ground, in a three-roller mill, with 36 g of hydrated alumina, 60 g of linseed-oil varnish of medium viscosity and 2 g of cobalt linoleate. The yellow printings produced with the formed dye paste are deeply coloured and have good fastness to light.

EXAMPLE 5

A polypropylene granulate suitable for producing fibres is thoroughly mixed with 2.5% of a pigment preparation containing 40% of a 1:2-nickel complex from the benzoylhydrazone of the formula VII. The mixture is spun at 240°–260° C. on a melt spinning machine into filaments, which are subsequently drawn in the ratio of 1:4 on a draw twister, and finally spooled. There is thus obtained a full yellow dyeing which is distinguished by good fastness to light, washing, dry-cleaning, exhaust gases and peroxide bleaching. There are likewise obtained very fast, yellow dyeings by using, with otherwise the same procedure, polycaprolactam granulate instead of polypropylene granulate, and spinning the mixture of 260°–290° C. into filaments.

The preparation used above is produced as follows: 40 parts of the yellow pigment, 60 parts of Mg-behenate and 500 parts of sodium chloride are thoroughly mixed in a powder mixer. This mixture is worked at 130° C. in a laboratory kneading machine; and the product obtained is subsequently ground with water, filtered, washed free from salt, dried and pulverised.

EXAMPLES 6 TO 35

There are likewise obtained fast yellow dyeings in plastics, lacquers, fibres or printing pastes when the procedure is carried out in a manner analogous to that of Examples 1 to 5 except that, in place of the pigment used therein, there is used a yellow 1:2-nickel complex of any one of the hydrazones listed in Tables 1 and 2.

TABLE 1

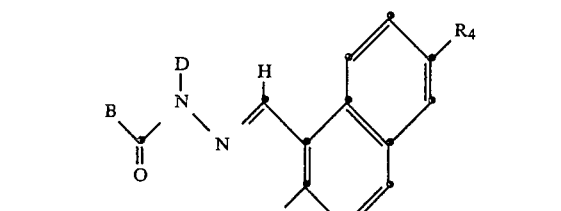

| Ex. No. | B | D | R₃ | R₄ |
|---|---|---|---|---|
| 6 | 4-Cl-phenyl | H | H | H |
| 7 | 4-CH₃-phenyl | H | H | H |
| 8 | 2-Cl-phenyl | H | H | H |
| 9 | 4-OCH₃-phenyl | H | H | H |
| 10 | 4-Br-phenyl | H | H | H |
| 11 | biphenyl | H | H | H |
| 12 | naphthyl | H | H | H |
| 13 | phenyl | H | H | Br |
| 14 | 4-OCH₃-phenyl | H | H | Br |
| 15 | 4-Cl-phenyl | H | H | Br |
| 16 | phenyl | H | COOH | H |
| 17 | 4-Cl-phenyl | H | COOH | H |
| 18 | phenyl | H | CONH-phenyl | H |
| 19 | phthalimido | | H | H |

TABLE 2

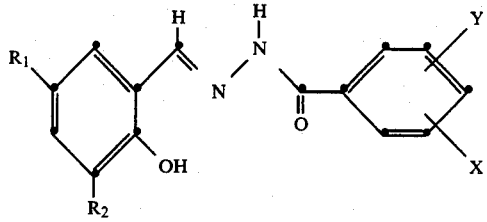

| Ex. No. | $R_1 = R_2$ | X | Y |
|---|---|---|---|
| 20 | Cl | H | H |
| 21 | Cl | 4-Cl | H |
| 22 | Cl | 4-CH$_3$ | H |
| 23 | Cl | 3-CH$_3$ | H |
| 24 | Cl | 4-OCH$_3$ | H |
| 25 | Cl | 3-Cl | H |
| 26 | Cl | 3-CH$_3$ | 4-CH$_3$ |
| 27 | Br | H | H |
| 28 | Br | 3-CH$_3$ | 4-CH$_3$ |
| 29 | Br | 4-CH$_3$ | H |
| 30 | Br | 3-Cl | H |
| 31 | Br | 4-OCH$_3$ | H |
| 32 | Br | 3-OCH$_3$ | 4-OCH$_3$ |
| 33 | Br | 4-Br | H |
| 34 | Br | 4-NO$_2$ | H |
| 35 | Br | 3-OCH$_3$ | 5-OCH$_3$ |

EXAMPLES 36 AND 37

Fast yellow dyeings in plastics, lacquers, fibres or printing pastes are also obtained by carrying out the procedure in a manner analogous to that of Examples 1 to 5 but by using, in place of the pigment used therein, a 1:2-nickel complex formed from a hydrazone of the formula

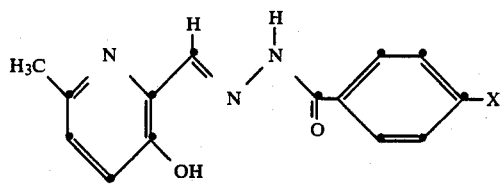

wherein X is hydrogen or chlorine.

EXAMPLE 38

5.1 g of 2-hydroxy-6-bromo-1-naphthaldehyde and 3.4 g of 4-chlorobenzoic acid hydrazide are stirred in 60 ml of acetic acid at 90° C. for 1 hour. There are then added 2.6 g of nickel acetate tetrahydrate, and the temperature is raised to 115° C. After being stirred for 3 hours, the mixture is filtered hot, and washed with alcohol. The yield after drying in vacuo at 60° C. is 3.7 g of a yellow 1:2-nickel complex of the hydrazone of the formula

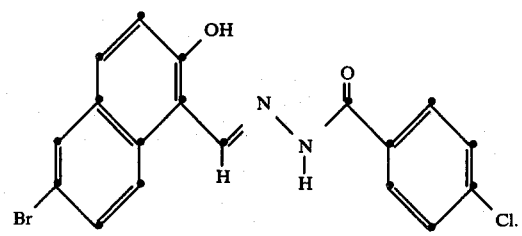

EXAMPLE 39

6.9 g of 2-hydroxy-1-naphthaldehyde and 6.8 g of 3-chlorobenzhydrazide are stirred in 50 ml of ethylene glycol monoethyl ether at 90° C. for 45 minutes. There are then added 5.2 g of nickel acetylacetonate, and stirring is maintained at 115° C. for 3 hours. The suspension is filtered hot, washed with ethanol, and dried at 60° C. in vacuo. The yield is 11.9 g of a yellow 1:2-nickel complex of the hydrazone of the formula

| Microanalysis | C % | H % | N % | Ni % |
|---|---|---|---|---|
| calculated | 61.4 | 3.15 | 7.9 | 8.3 |
| found | 60.7 | 3.6 | 7.8 | 8.1. |

EXAMPLE 40

5.6 g of 3,5-dibromosalicylaldehyde and 3.2 g of 3,4-dimethylbenzhydrazide are introduced into 60 ml of butanol, the mixture is heated to 90° C. and stirred for 30 minutes. There are then added 2.7 g of nickel acetylacetonate, and the mixture is stirred at 110° C. for 2 hours, and is subsequently filtered at 80° C.; the filter residue is then washed with alcohol, and afterwards dried at 70° C. in vacuo. The yield is 8.2 g of a yellow 1:2-nickel complex of the hydrazone of the formula

| Microanalysis | C % | H % | N % | Ni % |
|---|---|---|---|---|
| calculated | 42.3 | 2.9 | 6.2 | 6.5 |
| found | 43.1 | 3.1 | 6.9 | 6.7. |

EXAMPLE 41

17.2 g of 2-hydroxy-1-naphthaldehyde and 13.6 g of benzhydrazide are introduced into 200 ml of water. There are added 20 ml of ethanol and 5 ml of acetic acid; the mixture is then heated to 90° C., and is stirred for 90 minutes at this temperature. It is subsequently filtered and washed with water, and the product is dried at 50° C. in vacuo. The yield is 28.4 g of the benzoylhydrazone of the formula

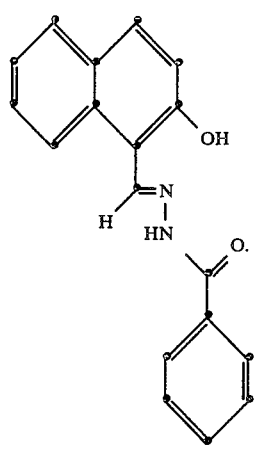

14.5 g of this benzoylhydrazone and 7 g of nickel acetate tetrahydrate are stirred in 150 ml of water at 90° C. for 4 hours. The yellow product is filtered, washed with water, and dried at 70° C. in vacuo. The yield is 14.8 g of a yellow 1:2-nickel complex of the benzoylhydrazone of the above formula.

EXAMPLE 42

10 g of titanium dioxide and 2 g of a ground 1:1-copper complex formed from benzoylhydrazone of the formula VII are incorporated into a lacquer in the manner described in Example 2; the lacquer is then sprayed onto aluminium sheet, preliminarily dried and subsequently stoved. The result is a full, greenish-yellow lacquer finish having very good fastness to over-lacquering, light and weather, and also a high gloss.

EXAMPLE 43

4 g of a ground 1:1-copper complex formed from the benzoylhydrazone of the formula VII, and 76 g of a lacquer mixture consisting of 41.3% of the 60% solution of a thermosetting polyacrylate (Viacryl VC 373 ®, Vianova, Austria) in xylene, 16.3% of the 55% solution of a melamine resin (Maprenal TTX ®, Cassella Farbwerke AG, Fed. Repub. of Germany) in butanol, 32.8% of xylene, 4.6% of ethylene glycol acetate, 2% of cyclohexanone, 2% of butyl acetate and 1% of a 1% silicone-oil solution in xylene, are dispersed for 72 hours in a ball mill.

8 g of the above mixture and 20 g of a 2% aluminium dispersion in paraffin and xylene are thoroughly mixed, and the mixture is uniformly sprayed onto sheet metal. After 30 minutes' preliminary drying, the spraying specimen is stoved at 120°–130° C. for 30 minutes. The result is a full, yellowish olive dyeing having very good fastness to weather.

EXAMPLES 44 TO 61

Further fast yellow dyeings in plastics, lacquers, fibres and printing pastes are obtained when the procedure is carried out in a manner analogous to that described in Examples 1 to 5 except that there is used, in place of the pigment used therein, the 1:1-metal complex of any one of the hydrazones listed in Table 3.

TABLE 3

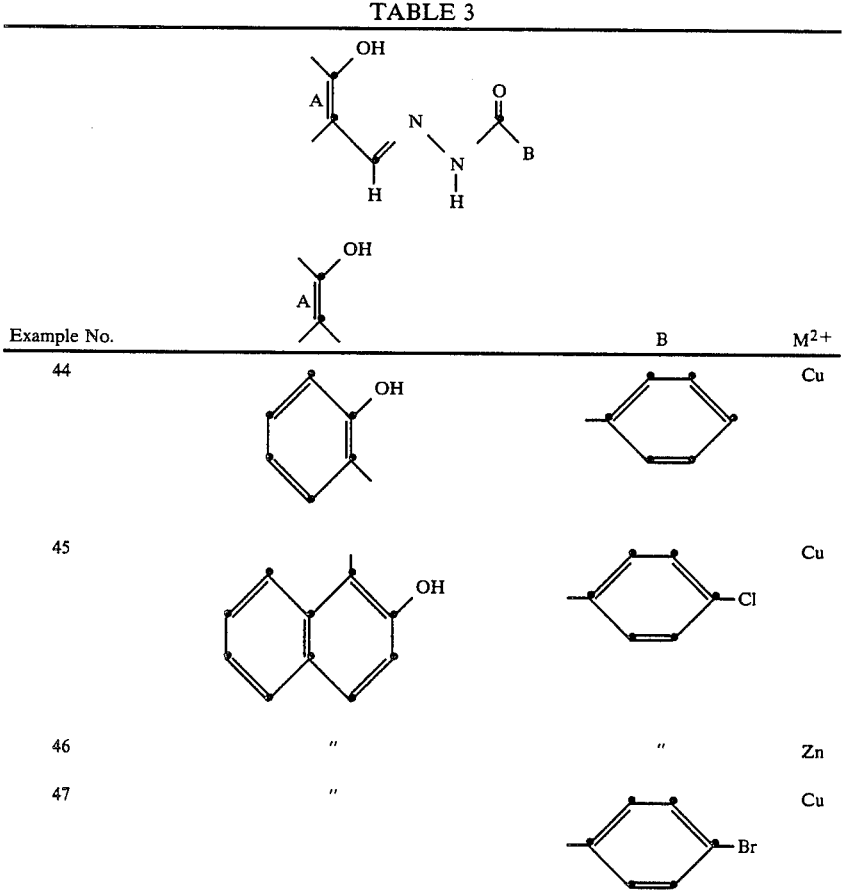

TABLE 3-continued
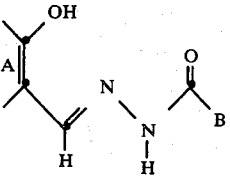
| Example No. | A-OH group | B | M²⁺ |
|---|---|---|---|
| 48 | " | 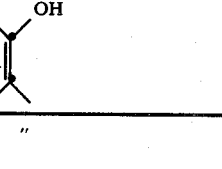 -CH₃ | Cu |
| 49 | " | 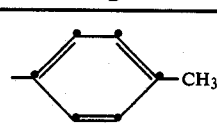 CH₃ | Cu |
| 50 | " | 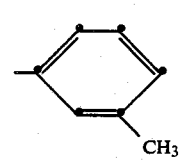 OCH₃ | Cu |
| 51 | " | 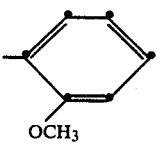 OCH₃, OCH₃ | Cu |
| 52 | " | 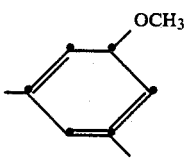 -NO₂ | Cu |
| 53 | 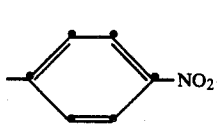 Br, OH | 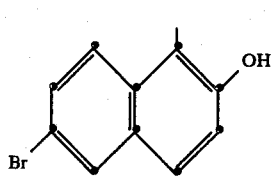 | Cu |
| 54 |  OH | 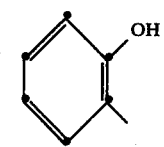 N | Ni |
| 55 |  O₂N, OH | " | Ni |

TABLE 3-continued
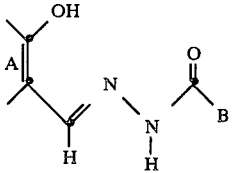
| Example No. | A | B | M²⁺ |
|---|---|---|---|
| 56 | 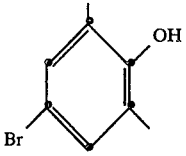 | " | Ni |
| 57 | 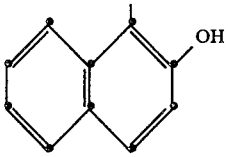 | " | Ni |
| 58 | 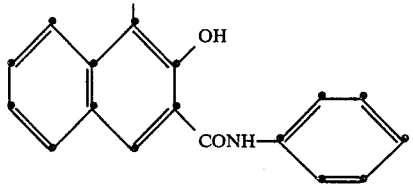 | " | Ni |
| 59 | 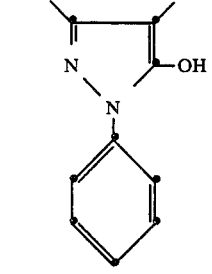 | 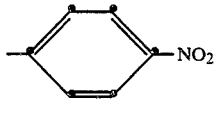 | Cu |
| 60 | 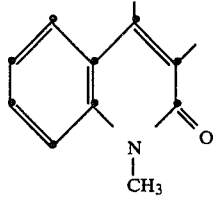 | 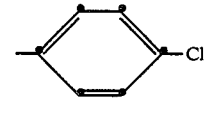 | Cu |
| 61 | " | " | Ni |
EXAMPLES 62 TO 66
Further fast yellow dyeings in plastics, lacquers, fibres and printing pastes are obtained by carrying out the procedure in a manner analogous to that of Examples 1–5 but using, instead of the pigment used therein, any one of the 1:1-metal complexes listed in Table 4.

Table 4

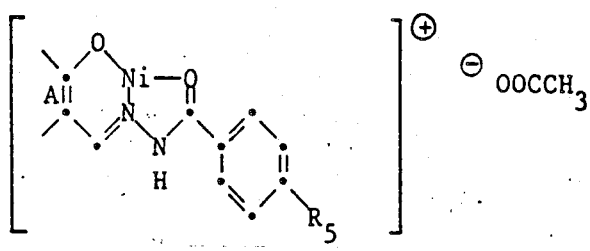

| | | |
|---|---|---|
| 62 | 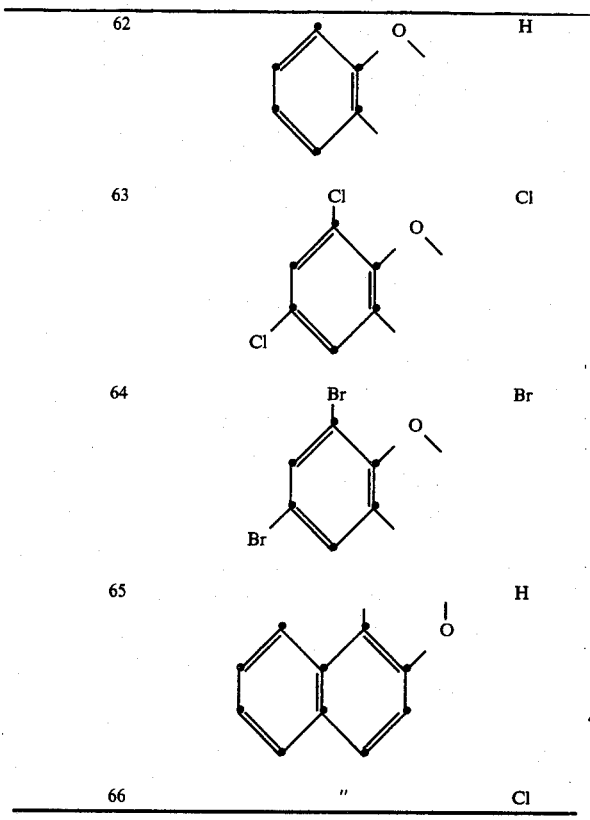 | H |
| 63 | | Cl |
| 64 | | Br |
| 65 | | H |
| 66 | " | Cl |

EXAMPLE 67

3.4 g of 2-hydroxy-1-naphthaldehyde and 2.7 g of benzhydrazide are condensed in 30 ml of ethylcellosolve at 100° C. for 30 minutes. After the addition of 5.2 g of nickel acetate tetrahydrate, the mixture is stirred at 120° C. for a further 4 hours. A yellow product precipitates; it is then filtered off, washed with ethanol, and dried at 80° C. in vacuo. The yield is 7 g of product containing crystal water, which product corresponds to the formula

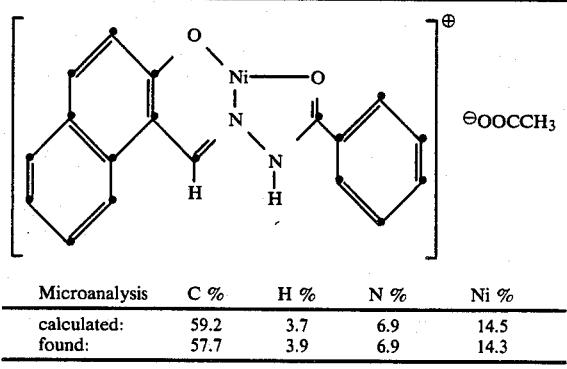

| Microanalysis | C % | H % | N % | Ni % |
|---|---|---|---|---|
| calculated: | 59.2 | 3.7 | 6.9 | 14.5 |
| found: | 57.7 | 3.9 | 6.9 | 14.3 |

EXAMPLE 68

1.72 g of 2-hydroxy-1-naphthaldehyde and 1.36 g of benzhydrazide are condensed in 40 ml of ethylcellosolve at 100° C. for 90 minutes. After the addition of 2.1 g of copper acetate monohydrate, the mixture is stirred at 110° C. for 3½ hours. The yellow product which has precipitated is filtered off at 60° C., washed with ethylcellosolve and ethanol, and dried at 80° C. in vacuo. The yield is 3 g of yellow pigment of the formula

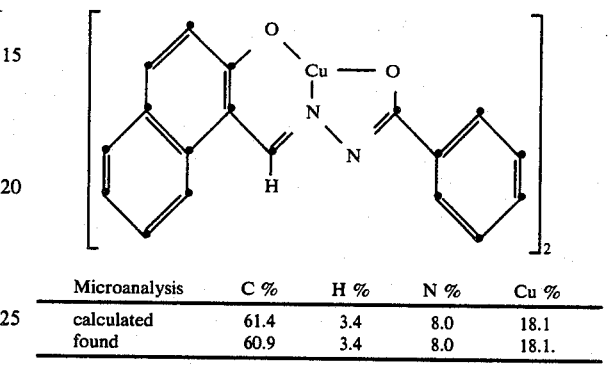

| Microanalysis | C % | H % | N % | Cu % |
|---|---|---|---|---|
| calculated | 61.4 | 3.4 | 8.0 | 18.1 |
| found | 60.9 | 3.4 | 8.0 | 18.1. |

What is claimed is:

1. A process for pigmenting high-molecular organic material, which comprises
incorporating therein a preformed transition-metal complex of a monohydrazone of the formula I

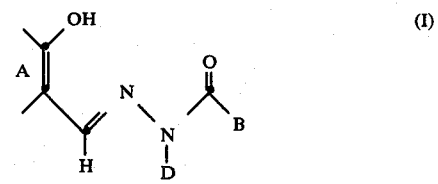 (I)

wherein A is an isocyclic or heterocyclic aromatic radical, B is a radical selected from the group consisting of unsubstituted or mono- or disubstituted benzene, naththalene, pyridine, pyrimidine, pyrazolone, quinoline, isoquinoline, pyrazole or coumarin where the substituents are halogen, $C_1$–$C_6$-alkyl, $C_1$–$C_6$-alkoxy, cyano, nitro, carboxy, $C_2$–$C_7$-alkoxycarbonyl, carbamoyl, phenyl, phenoxy, phenylcarbamoyl, benzoylamino, or phenyl, phenoxy, phenylcarbamoyl or benzoylamino each substituted by halogen, $C_1$–$C_6$-alkyl or $C_1$–$C_6$-alkoxy, and D is hydrogen, or if B is a phenyl or naphthyl group, D is hydrogen, or a carbonyl group which together with the structural element

forms a phthalimide or naphthalimide group.

2. A process according to claim 1 wherein the complex is a 1:2- or 1:1-nickel complex or the 1:1-copper complex of a hydrazone of the formula II

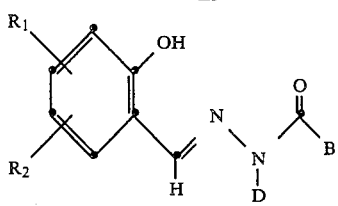

wherein $R_1$ and $R_2$ independently of one another are each hydrogen, chlorine, bromine, $C_1$–$C_3$-alkyl, $C_1$–$C_3$-alkoxy, cyano or nitro; B is phenyl or naphthyl, or said phenyl or said naphthyl substituted by one or two identical or different substituents selected from the group consisting of $C_1$–$C_3$-alkyl, $C_1$–$C_3$-alkoxy, chlorine, bromine, nitro, phenyl, phenoxy, chlorophenoxy, bromophenoxy, methylphenoxy, methoxyphenoxy, benzoylamino, methylbenzoylamino, methoxybenzoylamino, chlorobenzoylamino and bromobenzoylamino; and D is hydrogen, or a carbonyl group which together with the structural element

forms a phthalimide or naphthalimide group.

3. A process according to claim 2 wherein the complex is a 1:1- or 1:2-nickel complex or the 1:1-copper complex of a hydrazone of the formula II in which $R_1$ and $R_2$ independently of one another are each hydrogen, chlorine or bromine; B is phenyl or naphthyl, or said phenyl or said naphthyl substituted by one or two identical or different substituents selected from the group consisting of methyl, methoxy, chlorine, bromine, nitro or phenyl; and D is hydrogen.

4. A process according to claim 1 wherein the complex is a 1:1- or 1:2-nickel complex or 1:1-copper complex of a hydrazone of the formula III

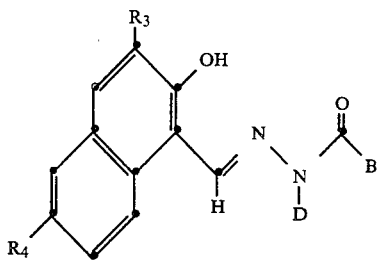

in which $R_3$ is hydrogen, carboxyl, $C_2$–$C_4$-alkoxycarbonyl, carbamoyl, or phenylcarbamoyl or said phenylcarbamoyl monosubstituted by $C_1$–$C_3$-alkyl, $C_1$–$C_3$-alkoxy, chlorine or bromine, and $R_4$ is hydrogen, chlorine, bromine or $C_1$–$C_3$-alkoxy; B is phenyl or naphthyl, or said phenyl or said naphthyl substituted by one or two identical or different substituents selected from the group consisting of $C_1$–$C_3$-alkyl, $C_1$–$C_3$-alkoxy, chlorine, bromine, nitro, phenyl, phenoxy, chlorophenoxy, bromophenoxy, methylphenoxy, methoxyphenoxy, benzoylamino, methylbenzoylamino, methoxybenzoylamino, chlorobenzoylamino and bromobenzoylamino; and D is hydrogen, or a carbonyl group which together with the structural element

forms a phthalimide or naphthalimide group.

5. A process according to claim 4 wherein the complex is a 1:1- or 1:2-nickel complex or 1:1-copper complex of a hydrazone of the formula III in which $R_3$ is hydrogen, carboxyl, methoxycarbonyl, carbamoyl or phenylcarbamoyl; $R_4$ is hydrogen or bromine; B is phenyl or naphthyl, or said phenyl or said naphthyl substituted by one or two identical or different substituents selected from the group consisting of methyl, methoxy, chlorine, bromine, nitro or phenyl; and D is hydrogen.

6. A process according to claim 2, wherein the complex is a 1:1- or 1:2-nickel complex or 1:1-copper complex of a hydrazone of the formula II in which $R_1$ and $R_2$ are chlorine; B is phenyl substituted by methyl; and D is hydrogen.

7. A process according to claim 4, wherein the complex is a 1:1- or 1:2-nickel complex or 1:1-copper complex of a hydrazone of the formula III in which $R_3$ is hydrogen, carboxyl or phenylcarbamoyl; $R_4$ is hydrogen or bromine; D is hydrogen; and B is phenyl or said phenyl monosubstituted by chlorine, bromine, methyl, methoxy or nitro.

8. A process according to claim 4, wherein the complex is a 1:1- or 1:2-nickel complex or 1:1-copper complex of a hydrazone of the formula III in which $R_3$, $R_4$ and D are hydrogen; and B is phenyl.

9. A process according to claim 2, wherein the complex is a 1:2-nickel complex of a hydrazone of the formula II.

10. A process according to claim 4, wherein the complex is a 1:2-nickel complex of a hydrazone of the formula III.

11. A process according to claim 6, wherein the complex is a 1:1-copper complex of a hydrazone of the formula II.

12. A process according to claim 4, wherein the complex is a 1:1-copper complex of a hydrazone of the formula III.

* * * * *